United States Patent
Raupach

(10) Patent No.: US 11,829,195 B2
(45) Date of Patent: Nov. 28, 2023

(54) METHOD FOR CHECKING A CHARACTERISTIC VARIABLE OF AN APPLICATION PROCEDURE OF AN X-RAY BASED MEDICAL IMAGING APPLICATION

(71) Applicant: Siemens Healthcare GmbH, Erlangen (DE)

(72) Inventor: Rainer Raupach, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 831 days.

(21) Appl. No.: 16/788,494

(22) Filed: Feb. 12, 2020

(65) Prior Publication Data
US 2020/0265177 A1    Aug. 20, 2020

(30) Foreign Application Priority Data
Feb. 20, 2019   (DE) .......................... 102019202287.1

(51) Int. Cl.
*A61N 5/10*    (2006.01)
*G06F 30/27*   (2020.01)
(Continued)

(52) U.S. Cl.
CPC ............. *G06F 30/27* (2020.01); *A61B 6/032* (2013.01); *A61B 6/5211* (2013.01);
(Continued)

(58) Field of Classification Search
CPC ........ G16H 50/50; G16H 30/40; G16H 30/20; A61B 6/032; A61B 6/5294;
(Continued)

(56) References Cited

U.S. PATENT DOCUMENTS

2002/0106054 A1   8/2002  Caflisch et al.
2004/0009459 A1   1/2004  Anderson et al.
(Continued)

FOREIGN PATENT DOCUMENTS

CN    103356224 A    10/2013
CN    103930036 A    7/2014
(Continued)

OTHER PUBLICATIONS

Ma, Yue et al: "The Monte Carlo Simulation of Tsinghua Homo-Source Dual-Beam Medical Accelerator" doi: 10.3969/j.issn. 1005-202X.2011.03.012 Chinese Journal of Medical Physics, May 2011 vol. 28 No. , (Key Laboratory of Particle & Radiation Imaging, Tsinghua University, Ministry of Education, Beijing 100084, China.

*Primary Examiner* — Don K Wong
(74) *Attorney, Agent, or Firm* — Harness, Dickey & Pierce, P.L.C

(57) ABSTRACT

A method is for checking a characteristic variable of an application procedure of an X-ray based medical imaging application, each patient model, of a plurality of patient models stored in a database, is characterized by at least one model parameter. In addition, a subset of the plurality of patient models is selected based upon the at least one model parameter assigned to a patient model or based upon the X-ray based medical imaging application. In addition, a number of simulated application procedures of the X-ray based imaging application are performed based upon the selected subset of patient models, at least one patient model being input into each performed simulated application procedure. Furthermore, a value of the characteristic variable is ascertained for each performed simulated application procedure. In addition, the value of the characteristic variable ascertained is output or is automatically evaluated based upon a specified target for the characteristic variable.

20 Claims, 7 Drawing Sheets

(51) Int. Cl.
*A61B 6/00* (2006.01)
*G16H 30/40* (2018.01)
*G16H 50/50* (2018.01)
*A61B 6/03* (2006.01)

(52) U.S. Cl.
CPC .......... *A61B 6/5288* (2013.01); *A61B 6/5294* (2013.01); *A61B 6/54* (2013.01); *G16H 30/40* (2018.01); *G16H 50/50* (2018.01)

(58) Field of Classification Search
CPC . A61B 2034/105; A61B 6/488; A61B 6/5211; A61B 6/5217; A61B 6/545
See application file for complete search history.

(56) References Cited

U.S. PATENT DOCUMENTS

| | | |
|---|---|---|
| 2004/0230404 A1 | 11/2004 | Messmer et al. |
| 2008/0292049 A1 | 11/2008 | Camus et al. |
| 2013/0267842 A1 | 10/2013 | Scheuering et al. |
| 2014/0343906 A1 | 11/2014 | Yagi et al. |
| 2015/0100290 A1* | 4/2015 | Falt ........................ G16H 50/50 703/2 |
| 2015/0100572 A1 | 4/2015 | Kalafut et al. |
| 2015/0164457 A1 | 6/2015 | Nett et al. |
| 2015/0347682 A1 | 12/2015 | Chen et al. |
| 2017/0095223 A1 | 4/2017 | Tian et al. |
| 2017/0228860 A1 | 8/2017 | Couch et al. |
| 2017/0344701 A1 | 11/2017 | Allmendinger |
| 2018/0032841 A1 | 2/2018 | Kluckner et al. |
| 2018/0189434 A1 | 7/2018 | Zhou et al. |
| 2018/0286515 A1 | 10/2018 | Hao et al. |
| 2019/0000325 A1 | 1/2019 | Dedroog et al. |
| 2019/0005647 A1 | 1/2019 | Hofmann |

FOREIGN PATENT DOCUMENTS

| | | |
|---|---|---|
| CN | 107423551 A | 12/2017 |
| CN | 107680657 A | 2/2018 |
| CN | 108268673 A | 7/2018 |
| CN | 108694999 A | 10/2018 |
| EP | 3363363 A1 | 8/2018 |

\* cited by examiner

METHOD FOR CHECKING A CHARACTERISTIC VARIABLE OF AN APPLICATION PROCEDURE OF AN X-RAY BASED MEDICAL IMAGING APPLICATION

PRIORITY STATEMENT

The present application hereby claims priority under 35 U.S.C. § 119 to German patent application number DE 102019202287.1 filed Feb. 20, 2019, the entire contents of each of which are hereby incorporated herein by reference.

FIELD

Embodiments of the invention generally relate to a method for checking a characteristic variable of an application procedure of an X-ray based medical imaging application, to a method for creating a database for checking a characteristic variable of an application procedure of an X-ray based medical imaging application, and also to a checking device, to a computer program product, and to a computer-readable storage medium.

BACKGROUND

X-ray based medical imaging applications form an integral part of daily clinical routine. Medical X-ray imaging using a computed tomography apparatus (CT apparatus), for instance, is a general example of an X-ray based medical imaging application. In this case, an X-ray tube generates the X-ray radiation that is used. The X-ray tube is mounted on a rotating assembly, which during operation of the CT apparatus performs a rotational movement about an axis along which is positioned the body region to be imaged of a patient. During the rotational movement of the X-ray tube, the X-ray detector is used to acquire projection measurement data for a plurality of angular directions. The projection measurement data is a projection, or a plurality of projections, containing information about the attenuation of the radiation by the subject under examination for each angular direction. Then two-dimensional cross-sectional image data or three-dimensional volumetric image data of the subject under examination can be reconstructed from this projection measurement data, for instance via a method known as filtered back-projection. A specific instance of an X-ray based medical imaging application in the context of CT imaging can then comprise, for example, cardiac imaging using a CT apparatus (cardiac CT) or a thorax CT. X-ray based medical imaging applications may also include other imaging techniques, for instance mammography imaging using a mammography apparatus, or radiography or angiography using a C-arm X-ray apparatus. X-ray based medical imaging applications can also be used in the treatment of a patient, for example for monitoring a treatment procedure.

As part of the optimization process for a procedure of an X-ray based medical imaging application, changes are often made, for example with the aim of improving the image quality, which also affect other characteristic variables of the application procedure, for instance the radiation dose given to a patient or the duration of the examination. This may potentially lead to conflicts with diagnostic reference levels (DRL) or targets set by the institution itself, i.e. the medical center.

Until now, the monitoring of important characteristic variables of an X-ray based imaging application, e.g. the dose distribution during a cardiac CT, would be performed mainly only retrospectively or only for specific operating points, e.g. regarding the dose modulation for a patient having a reference diameter. Although the former is always sensible for the purpose of quality assurance, it only uncovers problematic parameter settings in the application procedure relatively late. The latter constitutes a generalization and/or an oversimplification, with the result that for deviations from the reference or more complex cases, early detection of anticipated contraventions is only possible with difficulty.

SUMMARY

At least one embodiment of the invention provides an improved facility for checking a characteristic variable of an application procedure of an X-ray based medical imaging application.

The claims and the description below present further advantageous embodiments and developments of the invention, some of which are inventive in their own right.

The embodiments of the invention are described below with reference to the claimed method and with reference to the claimed device. Features, advantages or alternative embodiments mentioned in this connection can also be applied equally to the other claimed subject matter, and vice versa. In other words, the object-based claims (which claims are directed at a device, for example) can also be developed by combining with features described or claimed in connection with a method. The corresponding functional features of the method are embodied by corresponding physical modules or units.

At least one embodiment of the invention relates to a method for checking a characteristic variable of an application procedure of an X-ray based medical imaging application, comprising the steps of providing, selecting, performing, ascertaining, and outputting or automatic evaluation. In particular, the method can comprise both the outputting step and the automatic evaluation step.

An embodiment of the invention also relates to a method for creating a database for checking a characteristic variable of an application procedure of an X-ray based medical imaging application, comprising:

creating a plurality of patient models, each patient model of the plurality of patient models being characterized by at least one model parameter, wherein at least one of the patient models and the at least one model parameter of the associated patient model is based on clinical data from a real patient population; and storing the plurality of patient models created, in a memory.

An embodiment of the invention also relates to a checking device for checking a characteristic variable of an application procedure of an X-ray based medical imaging application, comprising a first interface, which is designed to provide a database, wherein the database comprises a plurality of patient models, and wherein each patient model is characterized by at least one model parameter, and comprising a processing unit. The processing unit is designed according to an embodiment of the invention to select a subset of the plurality of patient models on the basis of the at least one model parameter assigned to a patient model or on the basis of the X-ray based medical imaging application. The processing unit is also designed according to an embodiment of the invention to perform a number of simulated application procedures of the X-ray based imaging application on the basis of the selected subset of patient models, wherein at least one patient model of the selected subset is input into each performed simulated application procedure of the number of simulated application procedures. In addition, the processing unit is designed according to an embodiment of the invention to ascertain a value of the characteristic variable for each performed simulated application procedure of the number of simulated application procedures. Furthermore, the processing unit is also designed according to an embodiment of the invention to convey the ascertained value of the characteristic variable to another interface, or to evaluate automatically on the basis of a specified target for the characteristic variable, the value of the characteristic variable ascertained for each performed simulated application procedure.

A checking device according to an embodiment of the invention can be designed in particular to perform the above-described method according to an embodiment of the invention and the aspects thereof. The checking device can be designed to perform the methods and the aspects thereof by designing the interfaces and the processing unit to perform the relevant method steps.

In particular, an embodiment of the invention relates to a computer program product comprising a computer program, which can be loaded directly into a checking device, and which contains program segments, in order to perform all the steps of the method for checking a characteristic variable of an application procedure of an X-ray based medical imaging application, of an embodiment, when the program segments are executed by the checking device.

In particular, an embodiment of the invention relates to a computer-readable storage medium, on which are stored program segments which can be read and executed by a checking device in order to perform all the steps of the method for checking a characteristic variable of an application procedure of an X-ray based medical imaging application, of an embodiment, when the program segments are executed by the checking device.

In particular, an embodiment of the invention relates to a method for checking a characteristic variable of an application procedure of an X-ray based medical imaging application, the method comprising:
  providing a database via a first interface, the database including a plurality of patient models, each patient model of the plurality of patient models being characterized by at least one model parameter;
  selecting, via at least one processor, a subset of the plurality of patient models based upon the at least one model parameter assigned to a patient model or based upon the X-ray based medical imaging application;
  performing, via the at least one processor, a number of simulated application procedures of the X-ray based imaging application based upon the subset of patient models selected, wherein at least one patient model of the subset is input into each simulated application procedure of the number of simulated application procedures performed;
  ascertaining, via the at least one processor, a value of the characteristic variable for each simulated application procedure of the number of simulated application procedures performed; and
  outputting, via a second interface, the value of the characteristic variable ascertained for each simulated application procedure performed,
  or
  automatically evaluating, via the at least one processor, based upon a specified target for the characteristic variable, the value of the characteristic variable ascertained for each simulated application procedure performed, wherein the characteristic variable is checked based upon the outputting or based upon the automatic evaluating.

In particular, an embodiment of the invention relates to a method for creating a database for checking a characteristic variable of an application procedure of an X-ray based medical imaging application:
  creating a plurality of patient models, each patient model of the plurality of patient models being characterized by at least one model parameter, wherein at least one of the patient models and the at least one model parameter of the associated patient model is based on clinical data from a real patient population; and
  storing the plurality of patient models created, in a memory.

In particular, an embodiment of the invention relates to a checking device for checking a characteristic variable of an application procedure of an X-ray based medical imaging application, comprising:
  a first interface, designed to provide a database, the database including a plurality of patient models, each patient model of the plurality of patient models being characterized by at least one model parameter; and
  a processing unit, designed to:
  select a subset of the plurality of patient models based upon the at least one model parameter assigned to the patient model or based upon the X-ray based medical imaging application;
  perform a number of simulated application procedures of the X-ray based imaging application based upon the subset of patient models selected, at least one patient model of the selected subset being input into each simulated application procedure of the number of simulated application procedures performed;
  ascertain a value of the characteristic variable for each simulated application procedure performed, of the number of simulated application procedures; and
  convey the value of the characteristic variable ascertained, to a second interface,
  or
  automatically evaluate, based upon a specified target for the characteristic variable, the value of the characteristic variable ascertained for each performed simulated application procedure.

In particular, an embodiment of the invention relates to a checking device for checking a characteristic variable of an application procedure of an X-ray based medical imaging application, comprising:
  a first interface, designed to provide a database, the database including a plurality of patient models, each patient model of the plurality of patient models being characterized by at least one model parameter; and
  at least one processor, designed to:
  select a subset of the plurality of patient models based upon the at least one model parameter assigned to the patient model or based upon the X-ray based medical imaging application;
  perform a number of simulated application procedures of the X-ray based imaging application based upon the subset of patient models selected, at least one patient model of the selected subset being input into each simulated application procedure of the number of simulated application procedures performed;
  ascertain a value of the characteristic variable for each simulated application procedure performed, of the number of simulated application procedures; and convey the value of the characteristic variable ascertained, to a second interface, or automatically evaluate, based upon a specified target for the characteristic variable, the value of the characteristic variable ascertained for each performed simulated application procedure.

In particular, an embodiment of the invention relates to a non-transitory computer program product storing a computer program, directly loadable into a memory of a checking device, including program segments to perform the method of claim 1 when the program segments are executed by the checking device.

In particular, an embodiment of the invention relates to a computer-readable storage medium, storing program segments, readable and executable by a checking device to perform the method of claim 1 when the program segments are executed by the checking device.

BRIEF DESCRIPTION OF THE DRAWINGS

The invention is described below using example embodiments with reference to the accompanying figures. Schematic, highly simplified diagrams that are not necessarily to scale appear in the figures, in which.

DETAILED DESCRIPTION OF THE EXAMPLE EMBODIMENTS

Figure 1:
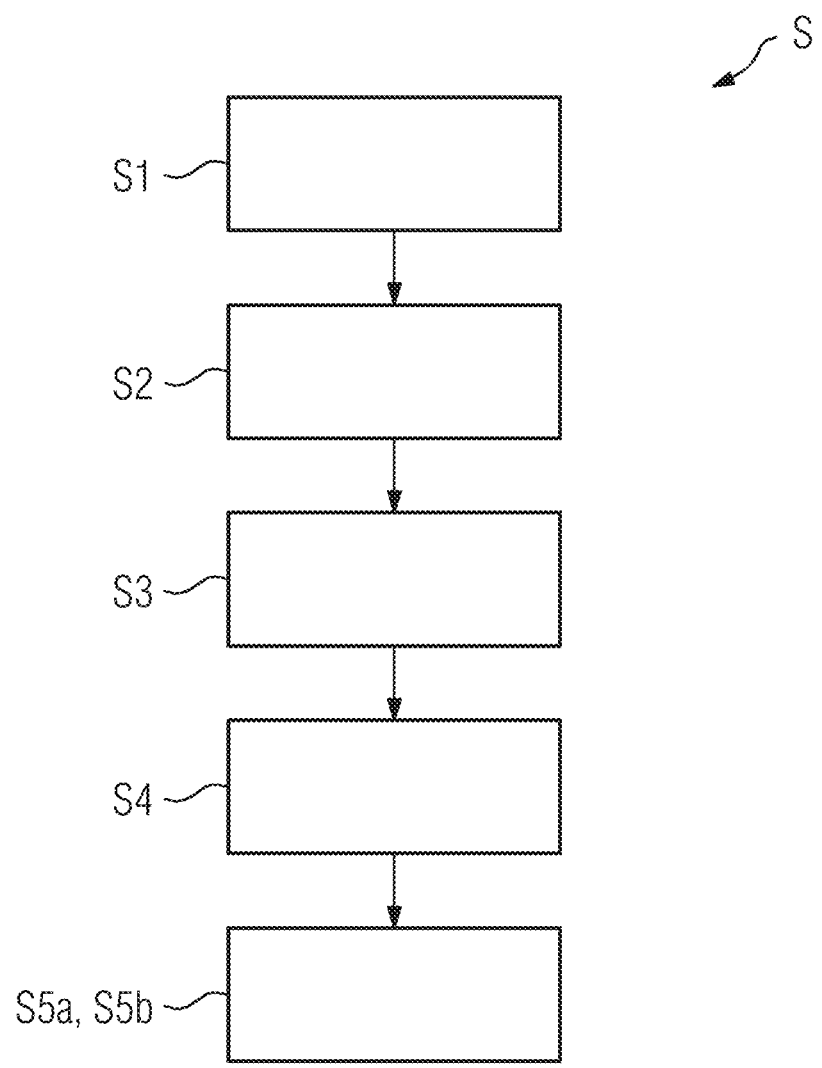
FIG. 1 shows an example flow diagram of a method for checking a characteristic variable of an application procedure of an X-ray based medical imaging application.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for checking a characteristic variable of an application procedure of an X-ray based medical imaging application, comprising the steps of providing, selecting, performing, ascertaining, and outputting or automatic evaluation. In particular, the method can comprise both the outputting step and the automatic evaluation step.

Conclusions about patient safety can be drawn from the characteristic variable under consideration. Conclusions about practical feasibility in the daily clinical routine or for the patient can be drawn from the characteristic variable under consideration. In principle, it is conceivable as part of the method according to an embodiment of the invention to check all the characteristic variables that previously were monitored during clinical use primarily retrospectively after applying the X-ray based imaging application. An example relating to an applied dose would be, for instance, the effective weighted CT dose index or the dose-length product. Another example of a characteristic variable can include the examination duration. For example, the characteristic variable includes the total duration of the X-ray based imaging application or the duration of sub-sequences of the X-ray based imaging application.

An X-ray based medical imaging application denotes in particular all imaging examinations as part of a patient treatment or diagnosis that is based on X-ray radiation. For instance, an X-ray based imaging application can include imaging using a CT apparatus. In particular, it can include a situation in which CT imaging is used, for example a cardiac CT, a head CT, or the like. It can also include, however, a different X-ray based application, for example an angiography application or a mammography application.

The application procedure of the X-ray based imaging application can also be referred to as a procedure protocol, examination protocol or scan protocol. The application procedure essentially defines the procedure of an X-ray based imaging application on a patient. The application procedure of the X-ray based imaging application can also comprise the procedure timing for the X-ray based imaging application. It can comprise in particular further parameters necessary to the procedure of the X-ray based imaging application that influence or characterize the application. These may be, for instance, settings or parameters of one or more apparatuses employed during the X-ray based imaging application. Parameters that influence or characterize the application procedure can also be referred to as application parameters. For example, by way of application parameters, the application procedure can comprise settings for an X-ray being used, start and end times for one or more successive exposures, a dependency of a patient-dependent value, parameters of the X-ray detector being used, time at which a contrast agent is injected, or the like.

In the providing step, a database is provided via an interface, wherein the database comprises a plurality of patient models. Each patient model of the plurality of patient models is characterized by at least one model parameter.

In advantageous embodiments of the invention, each patient model is characterized by a plurality of model parameters. It is thereby possible to allow modeling of a patient model that is as realistic and informative as possible. By virtue of a plurality of model parameters characterizing a patient model, it is possible in particular to provide greater differentiation between each patient model.

A patient model can be equivalent to a "virtual patient". This means that each of the patient models represents a potential patient of the X-ray based imaging application, and substantially describes one or more attributes of this patient that are essential to the X-ray based imaging application. In this sense, a model parameter can also be referred to as an attribute of the "virtual patient". A patient model in the database can be in the form of a complete patient model, which describes within the framework of a patient model the attributes of a "virtual patient" that are relevant to the X-ray based imaging application. It is also conceivable, however, that the patient models in the database describe the patient attributes in a "factorized form". This means that a multiplicity of partial patient models can be provided, which model only a selected subset of attributes of a "virtual patient". In this case, a "virtual patient", i.e. a complete patient model, can be produced by combining the patient models present in the database, i.e. the partial patient models.

A model parameter can represent an attribute of a patient to be examined by the X-ray based imaging application, which attribute is relevant to the X-ray based imaging application. For example, a model parameter can thus influence the application procedure, the characteristic variable to be checked, or the specified target. A model parameter can allocate a patient model also to a subgroup of patient models that have similarities in this model parameter. For example, a model parameter comprises an anatomical feature, a soft-tissue equivalent thickness, an ECG value, a test result, or an age of a "virtual patient". Other parameters are also conceivable, however.

In the selecting step, a subset of the plurality of patient models is selected by a processing unit on the basis of the at least one model parameter assigned to a patient model or on the basis of the X-ray based medical imaging application. The subset can also be selected on the basis of a combination thereof. In particular, the subset can also be selected on the basis of a combination of a plurality of model parameters. For example, the subset can be selected by way of an age assigned as a model parameter, via an anatomical feature, or via specific symptoms, which may be described by a test result, for instance.

The subset may comprise a single patient model. In advantageous embodiments of the method according to an embodiment of the invention, however, the subset comprises a plurality of patient models. A representative set of patient models is preferably selected from the database for an examination that is to be carried out, i.e. for the X-ray based imaging application under consideration. This can mean in particular that this step of the method preferably describes the real situation in the daily clinical routine, in which the typical patient collective, i.e. the typical patient population, may differ for different X-ray based imaging applications. A patient model can be assigned to a particular patient collective in particular on the basis of the at least one model parameter or the plurality of model parameters. The selection can be based, for example, also on the examination history of an X-ray based imaging application performed on real patients or on the examination history of a specific X-ray apparatus.

In the performing step, a number of simulated application procedures of the X-ray based imaging application are performed by the processing unit on the basis of the selected subset of patient models, wherein at least one patient model of the subset is input into each performed simulated application procedure of the number of simulated application procedures. This means that in the performing step, the processing unit simulates a number of application procedures on the basis of the selected patient models.

A simulated application procedure of the number of simulated application procedures can model in particular as realistic a procedure as possible of the X-ray based imaging application on a particular "virtual patient" of the selected subset. This can comprise in particular the startup timing. In particular here, the attributes of the particular "virtual patient" can be input as well. The attributes of the patient can influence the simulated application procedure. For example, it is possible to input the respiratory behavior from a respiratory curve or an ECG from the ECG readings, on the basis of which, simulated measurement sequences of the X-ray based imaging application can be controlled or adjusted. Anatomical features can influence, for example, the dimensions of the region under examination.

If the method according to an embodiment of the invention is used to check a characteristic variable that provides information about the dose applied to a patient, then as part of the performing, for example, software modules can be incorporated in the simulation of the application procedure that emulate the passage of X-rays through an object on the basis of the physical laws, and that simulate the absorption and scattering of X-rays by the object. Model parameters of a particular patient model that are input in this process can then allow the dose distribution to be modeled as accurately as possible. For example, anatomical features, the size, the diameter, soft-tissue equivalent thicknesses, or other model parameters can be input for this purpose.

The number of simulated application procedures can be determined in particular by the number of selected patient models. In particular, an application procedure of the X-ray based imaging application can be simulated for each "virtual patient" comprised by the selected subset. In expedient embodiments of the method according to the invention, a multiplicity of simulated application procedures are performed on the basis of a multiplicity of "virtual patients", with the result that the method can be used to model the patient collective typical as a whole of the X-ray based imaging application under consideration. The characteristic variable can hence be checked for the patient population typically occurring as a whole for an X-ray based imaging application or for an X-ray apparatus. Equally, however, the number of simulated application procedures can also comprise just one single simulated application procedure if the selected subset constitutes just one "virtual patient".

In the ascertaining step, a value of the characteristic variable is ascertained by the processing unit for each performed simulated application procedure of the number of simulated application procedures. In this process, a value of the characteristic variable under consideration is ascertained for each complete patient model, i.e. for each "virtual patient", based on the previously selected subset of patient models. If a plurality of application procedures are simulated for a plurality of "virtual patients", the associated plurality of ascertained values of the characteristic variable can reflect the variation or variance of the characteristic variable across the patient collective under consideration.

As part of the method, it is also possible in particular to check a plurality of characteristic variables by ascertaining a value for each of the plurality of characteristic variables for each performed simulated application procedure.

In the outputting step, according to an embodiment of the invention, for each performed simulated application procedure, the ascertained value of the characteristic variable is output via an interface. In particular, the output can be used to allow checking of the characteristic variable. For example, the ascertained value can be output to a memory unit and stored by the memory unit. On the basis of the stored value, the characteristic variable can advantageously be checked and/or also retained for checking and analysis at a later time. The value can also be output to a display unit, and displayed to a user in the form of a numerical value or as part of a displayed graph or the like. The viewer can thereby be given the facility to check the characteristic variable from the displayed value. On the basis of the display, measures can then be taken to prevent, for example, the X-ray based imaging application infringing regulatory targets. For instance, the application procedure can be adjusted.

As an alternative to, or in addition to, the outputting step, according to an embodiment of the invention, the value of the characteristic variable ascertained for each performed simulated application procedure can be evaluated automatically by the processing unit. The evaluation is based on a specified target for the characteristic variable. The automated evaluation facilitates a particularly simple check of the characteristic variable. In the case of a multiplicity of patient models and/or characteristic variables being considered, although not exclusively, this can improve the facility to assess and check the characteristic variable.

The specified target can be based on targets set on the basis of regulations by the user personally or by an institution itself, for instance a medical center. The specified target can comprise a specific value, i.e. a numerical value, for the characteristic variable. For instance, it can comprise a minimum value or a maximum value for the characteristic variable. The specified target can equally define a range of values for the characteristic variable. Such a range may define, for example, what range of values the characteristic variable can assume for the target still to be met. An example of a specified target would be, for instance, a maximum value for a dose indicator.

The evaluation can include establishing whether a value of the characteristic variable complies with the specified target for the characteristic variable or whether the ascertained value does not comply with the specified target. For example in the case of a specified target in the form of a maximum value, this means that there is compliance with the specified target as long as the ascertained value does not exceed the maximum value. The evaluation can also include a plurality of gradings. For instance, the evaluation can be based on a difference between the ascertained value and a specified target value, and be graded according to the value of the difference.

The inventors have discovered that the method according to an embodiment of the invention can advantageously reveal in good time, contraventions of specified targets and problems in the application procedure of an X-ray based imaging application. In particular, it is possible to check a characteristic variable before an actual application on a patient.

Until now, characteristic variables of an application procedure, e.g. the dose distribution as part of a cardiac CT, have been monitored in practice only retrospectively. In the case of the dose, for example, for a prospective appraisal, easy access to the behavior of the application procedure is generally possible only for specific operating points, e.g. for a patient with a reference diameter. The effect of patient sizes can also be determined by "examining" anthropomorphic phantoms, which takes a relatively large amount of time and effort. Even so, phantoms often constitute an oversimplification compared with real patients, and hence are not entirely representative. Taking into account the influence of other patient attributes is possible usually to a very limited extent, if at all. Apart from providing information about the behavior under "regular" and often idealized conditions, it is therefore difficult, if not impossible, to assess the dose and also other characteristic variables before an X-ray based imaging application is used in patient treatment. Similar considerations to those for the dose applied to a patient can also be made with regard to other indicators of the examination, for instance quantities such as scan times or the total examination duration. This is helpful in particular with regard to evaluating the practical feasibility of protocol changes.

In comparison with the current approach, the method according to an embodiment of the invention can be used advantageously to examine the behavior of the application procedure before the actual application on patients. This means that, unlike conventional, retrospective monitoring, the method according to an embodiment of the invention can be understood as a way of prospective monitoring of one or more characteristic variables, i.e. before any use of the X-ray based imaging application that potentially infringes guidelines or conflicts with practical aspects. Equally advantageously, the behavior of a characteristic variable even of application procedures that are complex or highly specific to each patient can be assessed in good time and time-efficiently. It is hence possible to improve the check of the characteristic variable in particular also for different patients, for instance patients who differ from a reference value. The method according to an embodiment of the invention also advantageously allows the characteristic variable to be checked efficiently for a complete, typical patient collective of an X-ray based imaging application, and not just at reference points. This is particularly desirable for patient safety as well as for the practical feasibility of an X-ray based imaging application in the daily clinical routine, in particular also when there are changes in the application procedure.

In particular, the characteristic-variable data obtained using the method according to an embodiment of the invention can be evaluated, displayed or stored just as in the conventional, retrospective monitoring process of a real examination. This advantageously allows the use of known software tools and evaluation processes, and allows communication of the characteristic-variable data in a manner familiar to a user.

In a variant of the method according to an embodiment of the invention, the method comprises the automatic evaluation step, wherein in the automatic evaluation step, a case of non-compliance with the specified target by the current ascertained value is determined on the basis of a comparison between the ascertained value and the specified target. This means that a comparison with the specified target is used to evaluate each of the ascertained values as to whether it complies with the specified target or whether it does not comply with the specified target, i.e. infringes the specified target. The comparison may include a mathematical operation, for instance forming a difference, a quotient or something else. A non-compliance case determined by the evaluation may also be referred to below as a problem case.

Advantageously, the method according to an embodiment of the invention efficiently detects in particular infringements of the specifications and targets.

In addition, in one embodiment, the method can also comprise the step of linking. In this step, the case of non-compliance of the current ascertained value of the characteristic variable is linked by the processing unit to the at least one model parameter of that patient model that has been input into the performed simulated application procedure forming the basis for the current ascertained value. This means that for a case in which an infringement of a target has been found, a connection is made between the non-compliance and the model parameter(s) underlying this case.

In particular, the linking comprises determining a correlation between the at least one model parameter and the non-compliance case. In other words, problem cases that arise are correlated with the attributes of the underlying patient model. For example, mathematical analysis can be used here to determine a numerical value for the correlation coefficient, i.e. a numerical value for the correlation occurring between a certain model parameter and the non-compliance case. In addition, a visual display of the linking can be used to allow a user to see or deduce the correlation, for instance from a graph.

A connection between one or more specific model parameters, i.e. patient attributes, and the infringement of targets can be made advantageously on the basis of the linking, or on the basis of the determined correlation. It is hence advantageously possible to ascertain one or more dominant influencing factors that may result in infringement of a specified target. A systematic analysis of the causes of the non-compliance can be achieved by linking and correlating the patient attributes input into the, possibly more than one, simulated application procedure with the non-compliance with the specified target. In particular, this can also advantageously serve as guidance to a user as to how improved compliance with the specified target can be achieved. Determining the correlation can allow dominant influencing factors on the compliance or non-compliance with a specified target to be ascertained informatively in particular when analyzing a multiplicity of ascertained values and the model parameters on which they are based.

It is also conceivable for problem cases that arise to be displayed on a display unit, for instance on a display, in association with the ascertained dominant influencing factor(s), so that the displaying can advantageously enable a user to draw conclusions about relevant subgroups of the virtual selected patient collective.

In a preferred variant of the method, the linking step comprises a machine learning technique or a cluster analysis technique.

Using a machine learning technique or in particular a cluster analysis technique is advantageously suited to ascertaining particularly efficiently a correlation between the non-compliance case and a specific model attribute and thereby dominant influencing factors.

A machine learning technique, or an artificial intelligence system, can refer to a system for artificially generating knowledge from experience. An artificial intelligence system learns from examples in a training phase, and can generalize once the training phase is finished. The use of the system can comprise recognizing patterns and regularities in the training data. After the training phase, the artificial intelligence system can extract features or associations in previously unknown data, for example. A cluster technique, also known as a cluster analysis technique, cluster analysis or clustering algorithms, is preferably used for the linking. These refer to techniques for detecting similarity structures or correlations in data pools. The groups of "similar" objects found in this way are referred to as clusters, and the assignment to groups as clustering. In cluster analysis, the aim is to identify new groups (also called clusters or classes) in the data, without the algorithm relying on prior knowledge of the classes. These new groups can then be used, for instance, for automatic classification, for pattern recognition or for data segmentation. Cluster analysis techniques are known in the prior art. A possible simple cluster technique is, for example, what is known as the k-means algorithm or DBSCAN algorithm (density-based spatial clustering of applications with noise).

The inventors have discovered that using a cluster analysis technique of this type, those cases, i.e. those simulated application procedures, in which the ascertained value of the characteristic variable has been found to infringe a target, can be correlated particularly well with the attributes of the underlying patient models in question. Dominant influencing factors can advantageously be ascertained in an automated and particularly efficient manner. Advantageously, a cluster analysis technique can be used to analyze efficiently in particular large amounts of data that can accrue in performing a multiplicity of application procedures, which in turn are each based on a patient model that may have a multiplicity of associated model attributes. Similarly, improvements can be made in detecting associations and connections in the data that are not obvious, or at least not readily obvious, to the user.

In an embodiment variant, the method according to an embodiment of the invention comprises the step of determining, via the processing unit, on the basis of the previously determined correlation, a proposed adjustment for adjusting at least one application parameter, which proposed adjustment predicts or assesses that a case of non-compliance with the specified target is prevented.

This can mean that, based on the determined correlation or a dominant influencing factor ascertained therefrom, a strategy or proposal is identified for changing one or more parameters in the application procedure under consideration in order to resolve a problem case that has arisen or to resolve at least some of a plurality of problem cases that have arisen. If a single simulated application procedure is the basis for the proposed adjustment, the aim of the proposed adjustment can be that, after adjustment of the application procedure by the proposed adjustment, an adjusted simulated application procedure is expected to result in compliance with the specified target. If a plurality of simulated application procedures are the basis for the proposed adjustment, the aim or prediction of the proposed adjustment can be that compliance with the specified target is predicted at least for a subset of simulated application procedures adjusted by the proposed adjustment. This means that in this case, a totality of the adjusted application procedures is predicted to have improved compliance with the specified target in that it is expected that at least one non-compliance case is prevented.

An application parameter in this context may be, for example, an operating parameter of an X-ray source being used, a scan parameter, for instance a duration or time instant of X-ray illumination, or suchlike. In particular, a plurality of proposed adjustments can be determined for one application parameter or for a plurality of application parameters.

The automated determination of a proposed adjustment can advantageously allow a rapid and systematic improvement in the application procedure of the X-ray based imaging application. In particular, a proposed adjustment determined by the processing unit can be used as guidance and relieving work for the clinical personnel. Decision processes can advantageously be improved or simplified. For this purpose, the proposed adjustment can be output to an output unit that facilitates the display for a user or user interaction.

According to a variant of the method according to an embodiment of the invention, the method also comprises the step of adjusting, via the processing unit, the application parameter on the basis of the proposed adjustment, and subsequent to the adjusting step, carrying out, on the basis of the adapted application procedure, repeatedly and successively in time, at least the performing step, the ascertaining step, and the automatic evaluation step.

In this variant of the method according to an embodiment of the invention, it is conceivable that the proposed adjustment is implemented in an automated manner without any intervention by a user being intended. It is equally possible for a user intervention to be intended. For example, a user can confirm a proposed adjustment or select a specific proposed adjustment from a plurality of proposed adjustments. After the intervention by the user, the proposed adjustment can then be implemented by the processing unit.

A number of simulated application procedures are then performed again on the basis of the adjusted application procedure, and a new value of the characteristic variable ascertained for each simulated application procedure. The value ascertained for each new simulated application procedure is then evaluated via the specified target. The re-evaluation can be used in particular to check whether the adjustment actually has led to improved compliance with the specified target.

This advantageously provides an opportunity for "prospective protocol optimization", in which specific aspects (e.g. relating to dose distribution, scan time, or suchlike) can be examined time-efficiently in the protocol optimization before clearance for the patient treatment. In particular, this can advantageously allow an iterative protocol optimization by carrying out the method steps repeatedly in succession, wherein the application procedure is adjusted successively until a defined termination condition is achieved. The termination condition can include that no problem case arises according to the criteria, i.e. according to the defined specified target(s). The termination condition can also include that the repetition loop can be made manually by a user according to the current status, i.e. the current evaluation of the ascertained value(s).

According to one embodiment, the method according to the invention can also comprise the step of storing, via a memory unit, the current ascertained value of the characteristic variable, or the evaluation of the current ascertained value, in association with that patient model that has been input into the performed simulated application procedure forming the basis for the current ascertained value.

For example in this step, the value of the characteristic variable or the evaluation thereof can be stored in association with the patient model concerned. This can be carried out in the same form as in real examinations, e.g. in the form of a DICOM SR (structured report) known in the prior art, specifically, related to the applied dose, for example in the form of a DICOM DoseSR. The simulated examination results and indicators of the X-ray based imaging application can hence be held in a particularly advantageous form, for instance for further analysis and use.

In another method variant, the method according to an embodiment of the invention also comprises the step of combining at least two patient models of the plurality of patient models into a combined patient model, and wherein in the performing step, the combined patient model is input as well into at least one simulated application procedure of the number of simulated application procedures.

In this embodiment variant, the patient models provided by the database do not describe a complete "virtual patient". Each patient model in the database then comprises patient attributes or model parameters that describe only a portion or a partial aspect of a "virtual patient". In other words, in this embodiment variant, the database provides the attributes of a "virtual patient" in a "factorized form". A complete patient model, i.e. a combined patient model or a "virtual patient", is then produced only by combining at least two or more partial patient models, so that in total all attributes of a "virtual patient" are described that are relevant to performing the application procedure. Each of such subsets can relate to, for instance, anatomical attributes, specific test results, respiratory curves, or cardiac parameters. By holding the patient attributes in this factorized form, advantageously fewer entries in the database are needed in order to model a larger patient collective.

According to one embodiment of the method according to the invention, the characteristic variable is a dose characteristic variable, which characterizes the X-ray based medical imaging application in terms of an applied radiation dose, or is a time characteristic variable, which characterizes a duration of the application procedure of the X-ray based medical imaging application or the duration of subunits of the application procedure of the X-ray based medical imaging application.

A dose characteristic variable can exist, for example, in the form of known indicators such as the effective weighted CT dose index (CTDIvol), the size-specific dose estimate (SSDE), the dose-length product (DLP), or suchlike. In particular, the applied dose is important with regard to the patient safety of an X-ray based imaging application. Therefore it is particularly desirable to have improved checking and monitoring of a dose indicator, in particular also before actually applying an application procedure of an X-ray based imaging application.

A time indicator can comprise, for example, scan times, i.e. for instance the time taken by a computed tomography apparatus to acquire the projection measurement data. These are relevant, for instance, to the time length for which the patients must hold their breath during thorax or cardiac imaging. The achievable patient throughput, for example, can be deduced from the total duration of the application procedure. The practical feasibility of an X-ray based imaging application can advantageously be checked.

According to another advantageous embodiment of the method according to the invention, the at least one model parameter of a particular patient model is based on clinical data of a patient. The clinical data comprises in particular a parameter from the following list: anatomical feature, soft-tissue equivalent thickness, cardiac parameter, ECG value, respiratory curve, test result, age of the patient. Other clinical data is also conceivable as well.

Realistic modeling of the virtual patient and hence of the application procedure is possible particularly advantageously by virtue of the model parameters being based on clinical measured data of a patient. This also advantageously allows a comparison of a value ascertained prospectively by the method and a value of a characteristic variable ascertained retrospectively in a measured examination. Mismatches or matches that arise can provide information about the quality of a simulated performance of the application procedure, about the quality of the database, or about the selection of the subset of patient models, and can be used to deduce improvements and optimizations.

In a method variant of the method according to the invention, in addition the selection of the subset of patient models, and/or the database, is optimized on the basis of a comparison of a value of the characteristic variable, which value is ascertained according to the invention, and a measured value of the characteristic variable.

In particular if there exist both a multiplicity of real examinations and a multiplicity of simulated application procedures on the basis of the virtual patient, these can be compared continuously with one another. The aim of the comparison can then be a match between simulated and real distribution of examination indicators, i.e. of the ascertained values of the characteristic variable. Assuming that the simulation actually ascertains the indicators of the real examination sufficiently accurately, then discrepancies can signify that the patient models present in the database, or selected in the selecting step, are not representative of the real patient collective. If differences are found, then the database or the selection for the specific examination can be optimized continuously, thereby minimizing the discrepancies. This can be realized technically, for example, by minimizing a cost function which describes the discrepancy in the dose distributions of the real and simulated datasets.

An embodiment of the invention also relates to a method for creating a database for checking a characteristic variable of an application procedure of an X-ray based medical imaging application, comprising the step of creating and storing.

In the creating step, a plurality of patient models are created, wherein each patient model of the plurality of patient models is characterized by at least one model parameter, and wherein the patient models and/or the at least one model parameter of the associated patient model are based on clinical data from a real patient population. In the storing step, the plurality of patient models is then stored by a memory unit.

One possible way of producing such a database is to compile initially X-ray based imaging applications that have actually been performed, and to extract the relevant parameters from available data, e.g. an ECG signal acquired during the examination, anatomical features etc. A dataset which characterizes a patient model can then be created from the measured data and stored.

Advantageously, a database can be produced that can be provided, via an interface, for a method according to the invention for checking a characteristic variable, and that can describe as realistic a patient population as possible of an X-ray based imaging application.

An embodiment of the invention also relates to a checking device for checking a characteristic variable of an application procedure of an X-ray based medical imaging application, comprising a first interface, which is designed to provide a database, wherein the database comprises a plurality of patient models, and wherein each patient model is characterized by at least one model parameter, and comprising a processing unit. The processing unit is designed according to an embodiment of the invention to select a subset of the plurality of patient models on the basis of the at least one model parameter assigned to a patient model or on the basis of the X-ray based medical imaging application. The processing unit is also designed according to an embodiment of the invention to perform a number of simulated application procedures of the X-ray based imaging application on the basis of the selected subset of patient models, wherein at least one patient model of the selected subset is input into each performed simulated application procedure of the number of simulated application procedures. In addition, the processing unit is designed according to an embodiment of the invention to ascertain a value of the characteristic variable for each performed simulated application procedure of the number of simulated application procedures. Furthermore, the processing unit is also designed according to an embodiment of the invention to convey the ascertained value of the characteristic variable to another interface, or to evaluate automatically on the basis of a specified target for the characteristic variable, the value of the characteristic variable ascertained for each performed simulated application procedure.

In a variant of the checking device according to an embodiment of the invention, in particular the processing unit is designed to determine, in the automatic evaluation, a case of non-compliance with the specified target by the current ascertained value on the basis of a comparison between the current ascertained value and the specified target. In addition, at least one application parameter can influence the application procedure of the X-ray based imaging application, and the processing unit is designed to link the case of non-compliance of the current ascertained value of the characteristic variable to the at least one model parameter of that patient model that has been input into the performed simulated application procedure forming the basis for the current ascertained value, wherein the linking comprises determining a correlation coefficient between the at least one model parameter and the non-compliance case. In this variant, the processing unit is also designed to determine on the basis of the determined correlation coefficient, a proposed adjustment for adjusting the at least one application parameter, wherein a case of compliance with the specified target by the current ascertained value of the characteristic variable by virtue of applying the proposed adjustment is predicted, and in addition the processing unit is designed to adjust the application procedure on the basis of the proposed adjustment.

A checking device according to an embodiment of the invention can be designed in particular to perform the above-described method according to an embodiment of the invention and the aspects thereof. The checking device can be designed to perform the methods and the aspects thereof by designing the interfaces and the processing unit to perform the relevant method steps.

In particular, an embodiment of the invention relates to a computer program product comprising a computer program, which can be loaded directly into a checking device, and which contains program segments, in order to perform all the steps of the method for checking a characteristic variable of an application procedure of an X-ray based medical imaging application, of an embodiment, when the program segments are executed by the checking device.

In particular, an embodiment of the invention can relate to a computer-readable storage medium, on which are stored program segments which can be read and executed by a checking device in order to perform all the steps of the method for checking a characteristic variable of an application procedure of an X-ray based medical imaging application, of an embodiment, when the program segments are executed by the checking device.

An implementation largely in software has the advantage that even checking devices already in use can be easily upgraded by a software update in order to work in the manner according to the invention. Such a computer program product may comprise in addition to the computer program, if applicable, extra elements such as e.g. documentation and/or extra components, and also hardware components such as e.g. hardware keys (dongles etc.) for using the software.

FIG. 1 shows a flow diagram of a method S for checking a characteristic variable of an application procedure of an X-ray based medical imaging application XRAY.

The method S shown comprises the steps of providing S1, selecting S2, performing S3, ascertaining S4, and outputting S5a or evaluation S5b.

In the providing step S1, a database DB is provided via an interface ST1, wherein the database comprises a plurality of patient models PM. Each patient model PM is characterized by at least one model parameter. In particular, the model parameter of a particular patient model comprises a parameter that can influence the application procedure, the ascertained value of the characteristic variable, or the specified target.

Each patient model PM can describe what is known as a "virtual patient". In the context of the example embodiment presented here, each patient model PM can be characterized in particular by a plurality of model parameters. This is a particularly preferred variant of the method according to an embodiment of the invention, allowing a "virtual patient" to be represented as realistically as possible and with greatest possible differentiation in its attributes. In addition, an application procedure simulated in the method according to an embodiment of the invention can hence be modeled as realistically as possible, and a value of the characteristic variable ascertained by the method can reflect the characteristic variable to be checked in the most informative way possible.

According to a variant of the method according to an embodiment of the invention, the model parameters of a particular patient model PM may be based in particular also directly on clinical, i.e. in particular measured, data from a real patient. This means that the database DB can comprise a patient model that represents an actual description of a real patient, and that bases the description of the real attributes of the patient on measured values from real examinations and measurements.

The clinical data can comprise in particular a parameter from the following list: anatomical feature, soft-tissue equivalent thickness, cardiac parameter, ECG value, respiratory curve, test result, or age of the patient. An anatomical feature may here relate to the skeleton structure, for instance. This can be input, for example, into the scan plan and the definition of a region to be imaged. It may relate to the size or girth of a patient. Just like the soft-tissue equivalent thickness, this can influence, for example, characteristic variables such as the duration of an application or the dose modulation, parameter settings of an apparatus being used, or the assignment to a patient collective. The ECG value may be part of an ECG curve that, just like the respiratory curve, is relevant to performing the application procedure for example for a cardiac CT or a thorax CT. Scan times and the procedure timing, for example, may be influenced thereby. A test result, for instance, can be used to demarcate a patient collective. The age of a patient can influence the specified target, for example. Other clinical data is also conceivable as well.

In the selecting step S2, a subset of the plurality of patient models PM is selected by a processing unit RH. This selection is made under consideration of the X-ray based medical imaging application and/or on the basis of the model parameters. This can ensure, for example, that the selected subset describes a specific case to be examined of the X-ray based imaging application, or that the selected subset is representative of the X-ray based imaging application. In this sense, the selected subsets of different X-ray based imaging applications considered in the method according to an embodiment of the invention can preferably also be different. By selecting a subset comprising a plurality of patient models, which subset is representative of the X-ray based imaging application, the characteristic variable can be checked for the typical patient collective, so that variations and variances of the characteristic variable across the patient collective can be incorporated in the check of the characteristic variable. In other embodiment variants, however, the method can be carried out also solely using one patient model. In other words, the presented method variant and also the following variants can be performed using a single "virtual patient" and equally using a plurality of "virtual patients".

In the performing step S3, a number of simulated application procedures of the X-ray based imaging application XRAY are performed by the processing unit RH. For the performing, at least one patient model PM of the selected subset is input into each of the simulated application procedures. This means that for each "virtual patient" comprised by the selected subset of patient models PM, the performing of the X-ray based imaging application is simulated on the basis of the associated patient model PM. In this process, the model parameter(s) of a patient model PM are preferably input as well into the simulation such that the simulated application procedure comprises as realistic a procedure as possible of the X-ray based imaging application. For example, known software modules can be used here to emulate the passage of X-rays through an object on the basis of the physical laws, and to simulate the absorption and scattering of X-rays by the object. Hence an applied dose can be assessed by way of the simulated application procedure. As realistic a simulation as possible of the procedure timing can be used, for example, to deduce a time indicator, for instance the total examination duration or the duration of sub-sequences of the application procedure. For instance, this can relate to the length of time for which a patient must hold his breath during a scan sequence. It is also possible to input information about a specific X-ray apparatus, for instance a detector sensitivity or a scan speed of a CT apparatus being used, or local circumstances for an X-ray based imaging application, in order to allow as realistic a simulation as possible of the application procedure. It is likewise possible to incorporate a realistic scan plan. This means, for example, that a definition of the body segment being examined by an imaging technique can be incorporated in the simulative performing. For this purpose, the region to be examined can be defined in the application procedure on the basis of anatomical landmarks. To this end, the model parameter of a patient model PM can comprise the anatomical landmarks. The patient model PM can comprise, for example, a corresponding list of the anatomical landmarks needed for this purpose.

In the ascertaining step S4, a value of the characteristic variable is ascertained by the processing unit RH for each performed simulated application procedure. For a plurality of virtual patients, a plurality of implementations of the X-ray based imaging application are accordingly simulated, and a corresponding plurality of values of the characteristic variable are determined. Ideally, the variation or variance of the characteristic variable across the patient collective under consideration is reflected in this case. If the characteristic variable is checked using a single "virtual patient", however, then accordingly only one value of the characteristic variable is ascertained.

The method and the described variants can be transferred readily also to checking a plurality of characteristic variables.

In a further step S5a, in a first alternative of the method S shown, the value of the characteristic variable ascertained for each simulated application procedure is output via a second interface ST2. The ascertained value can be output, for example, to a memory unit or to a display unit, and the stored or displayed value can be used to allow a check of the characteristic variable on the basis of the displayed value.

In a second alternative, in a step S5b, each ascertained value of the characteristic variable is evaluated automatically by the processing unit RH on the basis of a specified target for the characteristic variable, wherein the characteristic variable is checked on the basis of the evaluation. The specified target can be based on targets set on the basis of regulations by the user personally or by an institution itself, for instance a medical center. In particular, the specified target can also be defined as part of the method according to an embodiment of the invention. The specified target can comprise, for example, a specific value, i.e. a numerical value, or a value range for the characteristic variable. An example of a specified target would be, for instance, a maximum value, which must be complied with, for a dose indicator.

In an advantageous embodiment of the method S, the selection of the subset of patient models PM, and/or the database DB, is optimized on the basis of a comparison of the ascertained values of the characteristic variable and measured values of the characteristic variable. This can be done, for example, by storing the values ascertained by the method likewise in the database DB, in order to allow subsequent optimization. The aim of this optimization may be that the patient models PM that are present in the database DB or selected in the selecting step are representative of the real patient collective.

Figure 2:
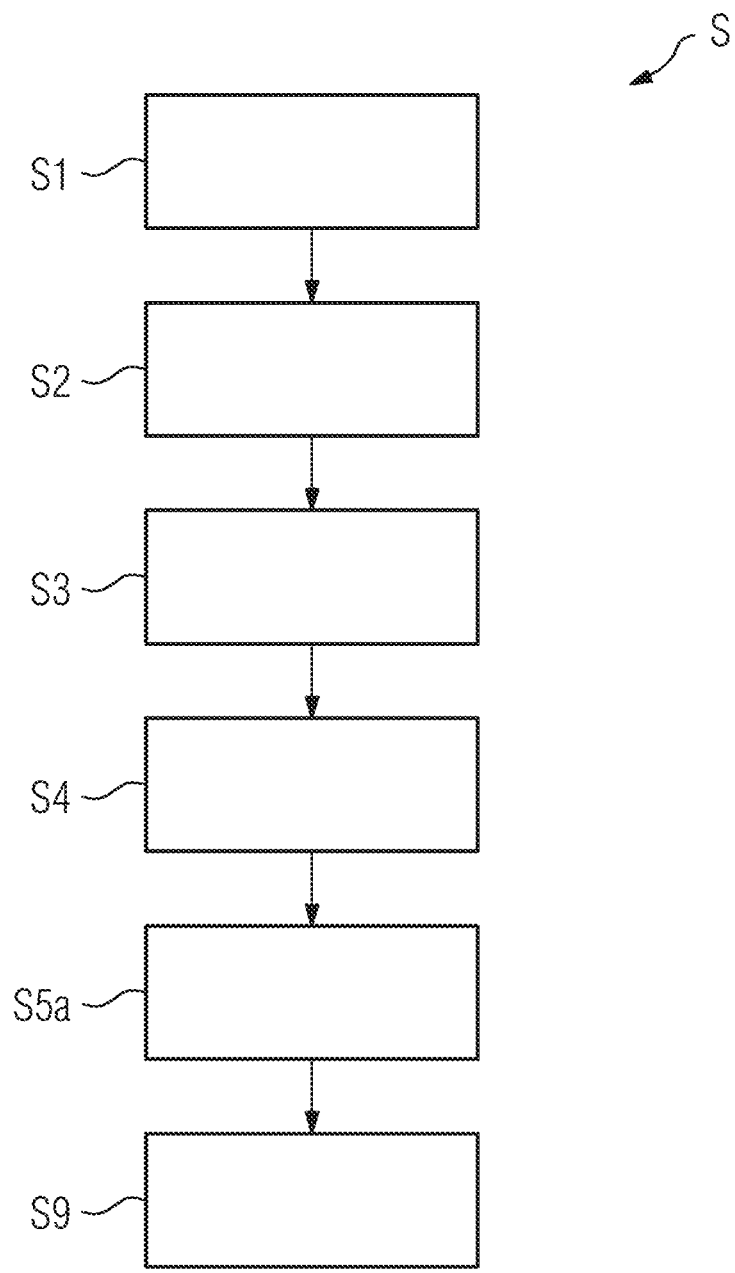
FIG. 2 shows a second example flow diagram of a method for checking a characteristic variable of an application procedure of an X-ray based medical imaging application.

FIG. 2 shows a further flow diagram of a method S for checking a characteristic variable of an application procedure of an X-ray based medical imaging application XRAY. The method variant shown comprises, in addition to the steps of providing S1, selecting S2, performing S3, and ascertaining S4, the step of outputting S5a and also the step of storing S9.

In the case of a plurality of ascertained values, the values of the characteristic variable ascertained for each simulated application procedure are output to a memory unit MU via a second interface ST2. In this case, the current ascertained value of the characteristic variable can be stored in association with that patient model PM that has been input into the performed simulated application procedure forming the basis for the current ascertained value. This can be implemented in the same form as in a real examination, e.g. in the form of a DICOM SR (structured report) known in the prior art, specifically, for example, in the form of a DICOM DoseSR. Provided the underlying patient model PM is based on the attributes of a real patient, the patient model PM, and hence also the simulated examination result obtained from a simulated application procedure, which result is in the form of the ascertained value(s), can be encoded in this case by way of the patient name, for example. This data produced by the virtual examinations, however, is advantageously kept at least distinguishable from the data of the real examinations, in order to be able to perform the monitoring process of the actual examinations separately.

Figure 3:
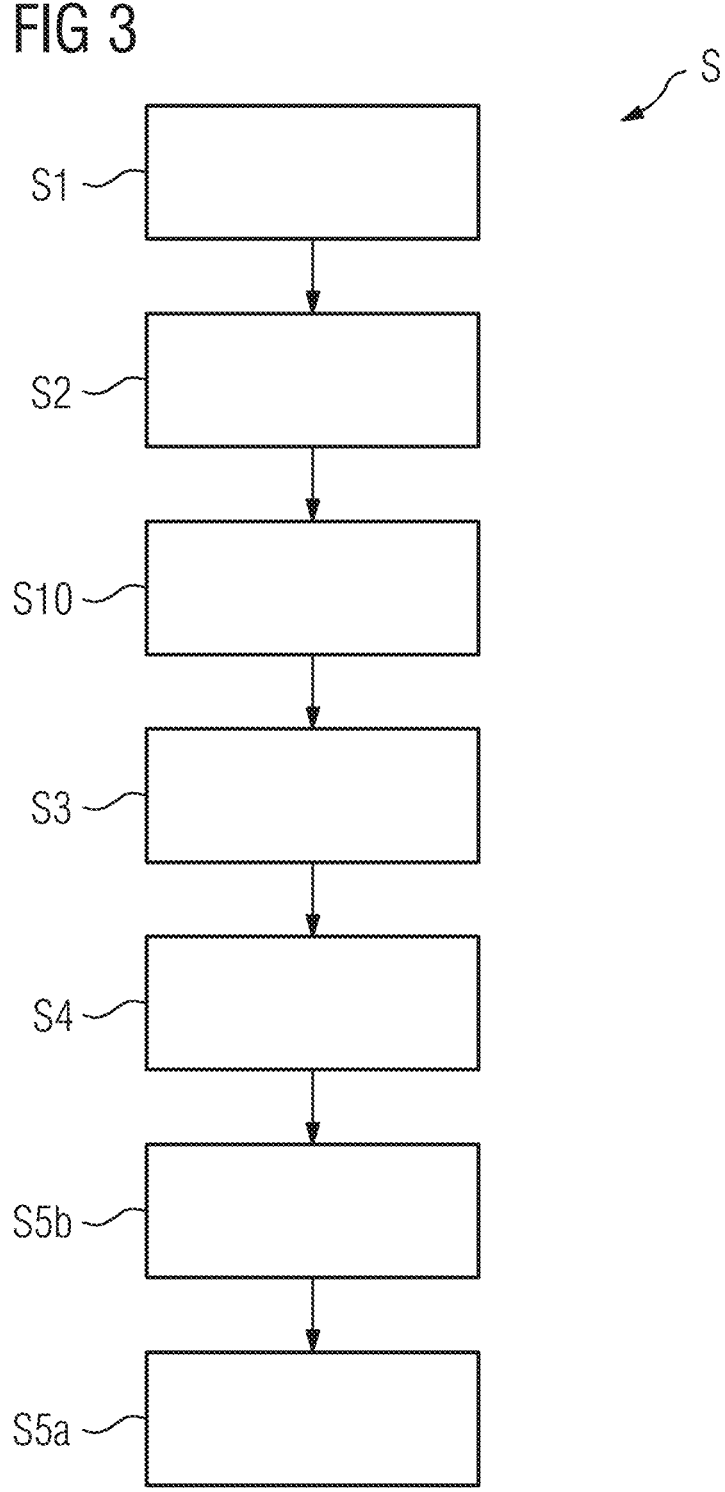
FIG. 3 shows a third example flow diagram of a method for checking a characteristic variable of an application procedure of an X-ray based medical imaging application.

FIG. 3 shows a further example flow diagram of a method S for checking a characteristic variable of an application procedure of an X-ray based medical imaging application XRAY. The variant shown comprises both the evaluation step S5b and the outputting step S5a. In the outputting step S5a, the ascertained values can be output together with the evaluation, for instance for visual display for a user on a display unit.

In addition, the variant shown comprises the step of combining S10. In this case, the database DB comprises patient models PM in what is known as a "factorized form". The provided patient models PM are partial patient models PM in this case. This means that each patient model PM in the database DB comprises patient attributes or model parameters that describe only a portion of a "virtual patient". A complete patient model, i.e. a combined patient model or a "virtual patient", is then produced in the combining step S10 only by combining at least two or more partial patient models PM, so that in total the attributes of a "virtual patient" are described that are relevant to performing the application procedure. Such subsets of model parameters provided by a partial patient model PM can each relate to e.g. anatomical attributes of a patient, specific test results for a patient, respiratory curves of a patient, cardiac parameters or other parameters of a patient. By holding the patient attributes in this factorized form, advantageously fewer entries in the database DB are needed in order to model a larger patient collective.

Figure 4:
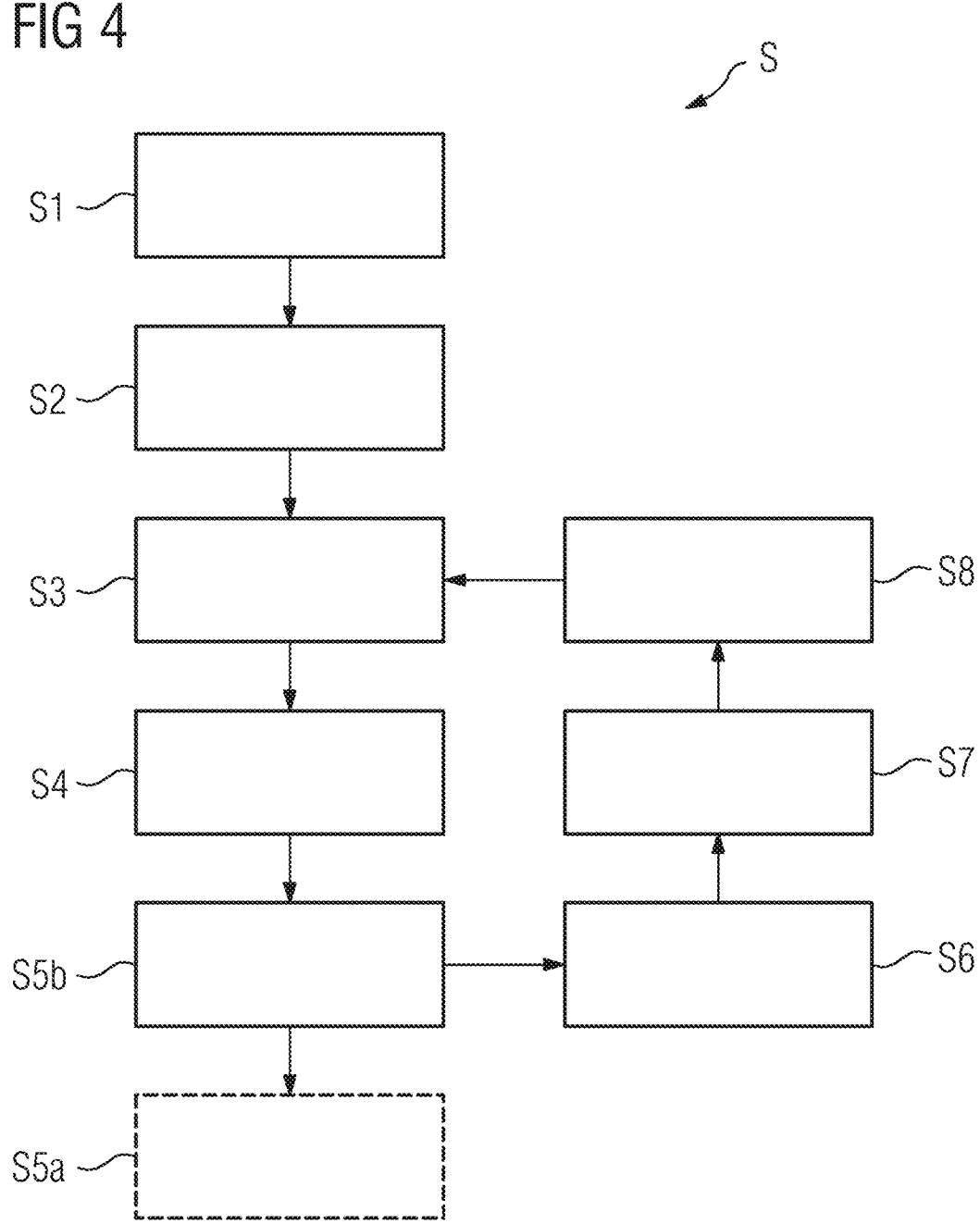
FIG. 4 shows a fourth example flow diagram of a method for checking a characteristic variable of an application procedure of an X-ray based medical imaging application.

FIG. 4 shows a further example flow diagram of a method S for checking a characteristic variable of an application procedure of an X-ray based medical imaging application XRAY. In particular, FIG. 4 shows a variant of the method S that allows an iterative prospective protocol optimization. It is assumed in this case that the application procedure of the X-ray based medical imaging application XRAY can be adjusted, i.e. can be influenced or changed, by at least one application parameter.

In this case, the evaluation step S5b includes that a case of non-compliance with the specified target by the current ascertained value is determined on the basis of a comparison between the ascertained value and the specified target. This means that for the number of simulated performances of the application procedure, what are known as problem cases are determined, which are cases in which a specified target is infringed, for instance a previously defined maximum value is exceeded.

After the evaluation step S5b, the step of linking S6 is subsequently performed by the processing unit RH. In the linking step S6, the case of non-compliance of the current ascertained value of the characteristic variable is linked to the at least one model parameter of that patient model PM that has been input into the performed simulated application procedure forming the basis for the current ascertained value. This means that given a plurality of simulated application procedures, each case of simulated performances in which the infringement of a target has been found is linked to, in particular correlated with, the attributes of the patient model PM underlying that case. The correlation can then be used, for example, to ascertain in particular dominant influencing factors in the simulated application procedures that lead to infringement of a target.

In an advantageous embodiment, the linking S6, or in particular the correlation, comprises a cluster analysis technique. The aim of such a technique is to identify new groups (also called clusters or classes) in data, without the algorithm relying on prior knowledge of the classes. A number of cluster analysis techniques from the field of machine learning that can be used as part of the invention in the linking step are known in the prior art.

Subsequently in the method S shown, in a step of determining S7, a proposed adjustment is determined by the processing unit RH for adjusting the at least one application parameter. The proposed adjustment is based here in particular on the previously determined correlation. The aim of determining the proposed adjustment is in particular to achieve improved compliance with the specified target by preventing at least one non-compliance case. This means that the prediction can include an assessment that, after another cycle of the method, an application procedure adjusted by the proposed adjustment achieves improved compliance with the specified target. For a plurality of ascertained values under consideration, this can mean in particular that improved compliance with the specified targets by at least some of the "virtual patients" under consideration is predicted, and hence it is expected that at least some of the problem cases can be resolved.

Subsequently in the method variant shown, in the step of adjusting S8, the at least one application parameter of the application procedure is adjusted by the processing unit RH on the basis of the previously determined proposed adjustment. The steps of performing S3, ascertaining S4 and evaluation S5b are then performed on the basis of the adjusted application procedure. This means that after the adjusting, a number of adjusted simulated application procedures are performed, and a new value for the characteristic variable is ascertained and evaluated on the basis of each. Any improvement that has occurred regarding compliance with the specified target can be monitored by the re-evaluation. If applicable, the result of the evaluation or the new ascertained value(s) are output via the second interface ST2. For instance, the interface ST2 can facilitate an output to a display unit and hence visualization for a user.

The loop of the steps of linking S6, determining S7, adjusting S8, performing S3, ascertaining S4, and evaluation S5b can, however, also be repeatedly executed until, for example, a previously defined termination condition is achieved. The termination condition can be applied in an automated manner by the processing unit RH. The termination condition may be, for instance, complete prevention of a problem case according to the check of the characteristic variable on the basis of the selected subset. In addition to an automated termination on the basis of a previously defined termination condition, it is also possible to allow a user to intervene and manually close the iteration loops. This can be achieved, for example, by outputting via the second interface ST2, and displaying, for instance via a display unit, interim states of the ascertained value(s) or of the evaluation. Once the termination condition has been achieved, or after a manual termination, the final state of the ascertained data can be output via the second interface ST2.

Figure 5:
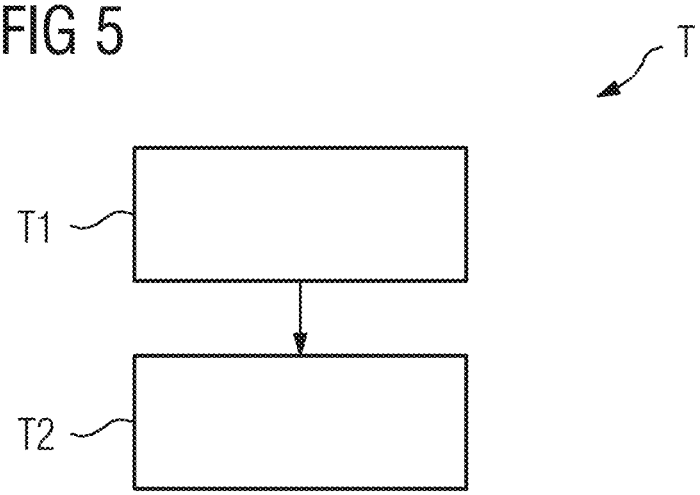
FIG. 5 shows an example flow diagram of a method for creating a database.

FIG. 5 shows an example flow diagram of a method for creating a database DB.

In the creating step, a plurality of patient models PM are created, wherein each patient model PM of the plurality of patient models PM is characterized by at least one model parameter, and wherein the patient models PM and/or the at least one model parameter of the associated patient model PM are based on clinical data from a real patient population.

In the storing step, the plurality of patient models PM are then stored by a memory unit. The stored patient models can then form the database for checking a characteristic variable of an application procedure of an X-ray based medical imaging application XRAY. It is conceivable here to add patient models PM continuously to the database DB by the database DB continuously receiving clinical data from patients. In this case, new patient models PM can be created on the basis of the new data, and stored. Likewise, new measured values and examinations can be used as the basis for additions or modifications to already stored patient models PM.

Figure 6:
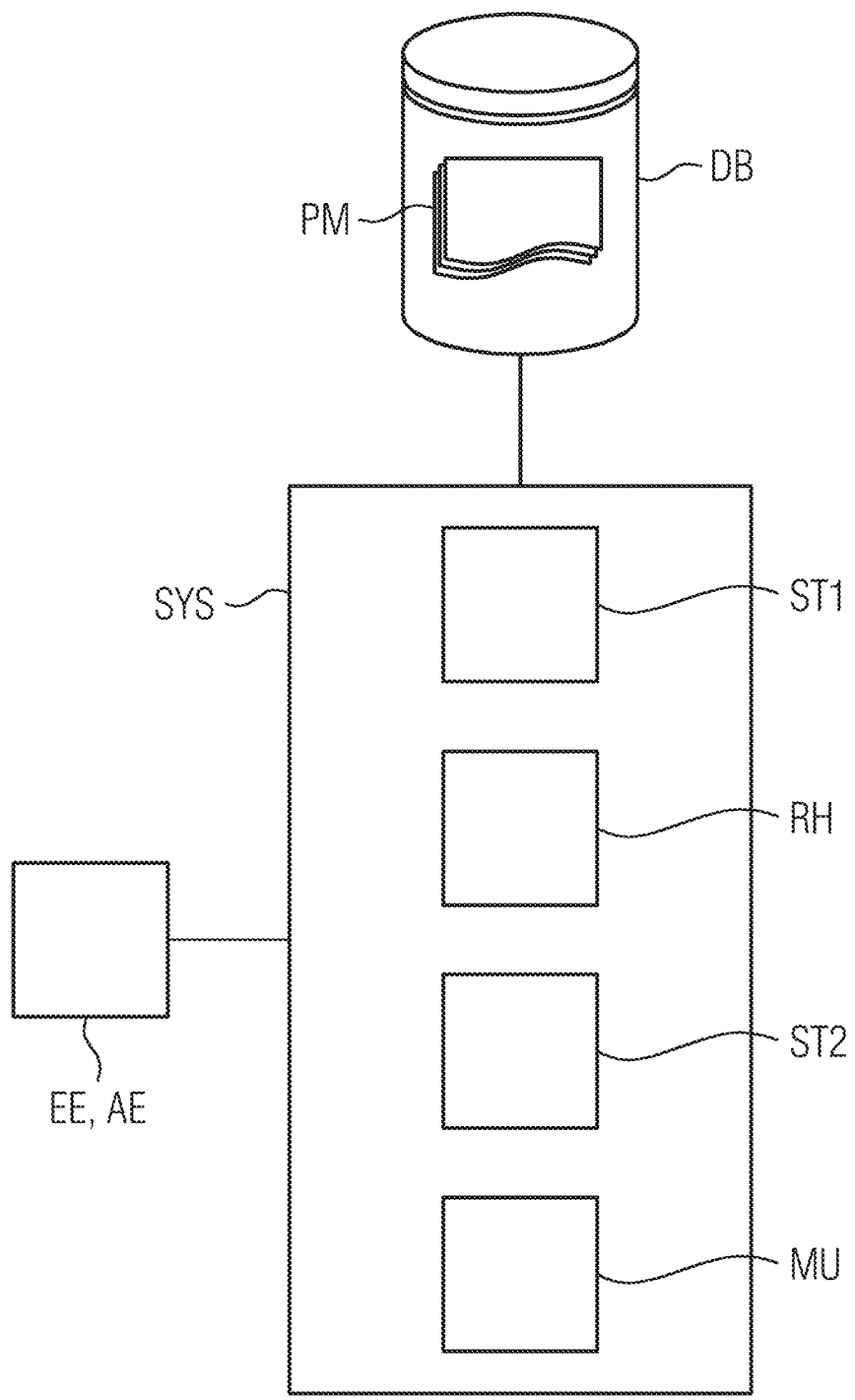
FIG. 6 shows a schematic example embodiment of a checking device.

FIG. 6 shows a schematic example embodiment of a checking device. The checking device comprises a first interface ST1. The first interface ST1 is designed to provide a database DB, wherein the database DB comprises a plurality of patient models PM, and wherein each patient model PM is characterized by at least one model parameter. The checking device also comprises a processing unit RH, wherein the processing unit RH is designed to select a subset of the plurality of patient models PM on the basis of the at least one model parameter assigned to a patient model PM or on the basis of the X-ray based medical imaging application XRAY. The processing unit RH is also designed to perform a number of simulated application procedures ABL of the X-ray based imaging application on the basis of the selected subset of patient models PM, wherein at least one patient model of the selected subset is input into each performed simulated application procedure of the number of simulated application procedures. In addition, the processing unit RH is designed to ascertain a value of the characteristic variable for each performed simulated application procedure of the number of simulated application procedures. The processing unit RH is also designed to convey the ascertained value of the characteristic variable to another interface ST2, and/or the processing unit RH is designed to evaluate automatically on the basis of a specified target for the characteristic variable, the value of the characteristic variable ascertained for each performed simulated application procedure.

The checking device SYS may be in particular a computer, a microcontroller or an integrated circuit. Alternatively, the checking device SYS may be a real or virtual interconnection of computers (a real interconnection is referred to as a "cluster" and a virtual interconnection is referred to as a "Cloud").

The checking device comprises a memory unit MU. This may be implemented as a non-permanent main memory (random access memory or RAM for short) or as a permanent mass storage device (hard disk, USB stick, SD card, solid state disk). An interface ST1, ST2 may be a hardware or software interface (for instance PCI bus, USB or FireWire). A processing unit RH may comprise hardware elements or software elements, for instance a microprocessor or what is known as a field programmable gate array (FPGA).

Optimally, the checking device SYS can also comprise an input and output unit, wherein an input and output unit comprises at least one input unit EE and/or at least one output unit AE. An ascertained value, an evaluation of an ascertained value, or the problem cases can be visualized via the output unit AE in the form of a display unit, for instance a display. An input unit allows, for instance, manual interaction by a user, for example terminating a protocol optimization, selecting a proposed adjustment, or changing a procedure parameter.

The database DB may likewise be a computer, a microcontroller or an integrated circuit. Alternatively, the database DB may be a real or virtual interconnection of computers (a real interconnection is referred to as a "cluster" and a virtual interconnection is referred to as a "Cloud"). The database DB may in particular comprise a memory unit that is suitable for storing the patient models and retaining the patient models for the purpose of providing. This may be implemented as a non-permanent main memory (random access memory or RAM for short) or as a permanent mass storage device (hard disk, USB stick, SD card, solid state disk).

The checking device SYS can be connected to the database DB via a network. In an alternative embodiment, however, the database DB can also be designed to be part of the checking device SYS. A network may be a local area network (LAN) or a wide area network (WAN). An example of a local area network is an intranet; an example of a wide area network is the Internet. The network can be implemented in particular wirelessly, in particular as a WLAN (wireless LAN, commonly known as WiFi) or as a Bluetooth connection. The network can also be implemented as a combination of the examples mentioned.

The checking device SYS shown can also be designed to determine, in the automatic evaluation, a case of non-compliance with the specified target by the current ascertained value on the basis of a comparison between the current ascertained value and the specified target, and to link the non-compliance case of the current ascertained value of the characteristic variable to the at least one model parameter of that patient model PM that has been input into the performed simulated application procedure forming the basis for the current ascertained value. The linking comprises determining a correlation between the at least one model parameter and the non-compliance case.

Provided the application procedure of the X-ray based imaging application XRAY can be influenced by at least one application parameter, the processing unit can also be designed to determine on the basis of the determined correlation, a proposed adjustment for adjusting the at least one application parameter, wherein a case of compliance with the specified target by the current ascertained value of the characteristic variable by virtue of applying the proposed adjustment is predicted. In this case, the processing unit RH can also be designed to adjust the application procedure on the basis of the proposed adjustment.

Figure 7:
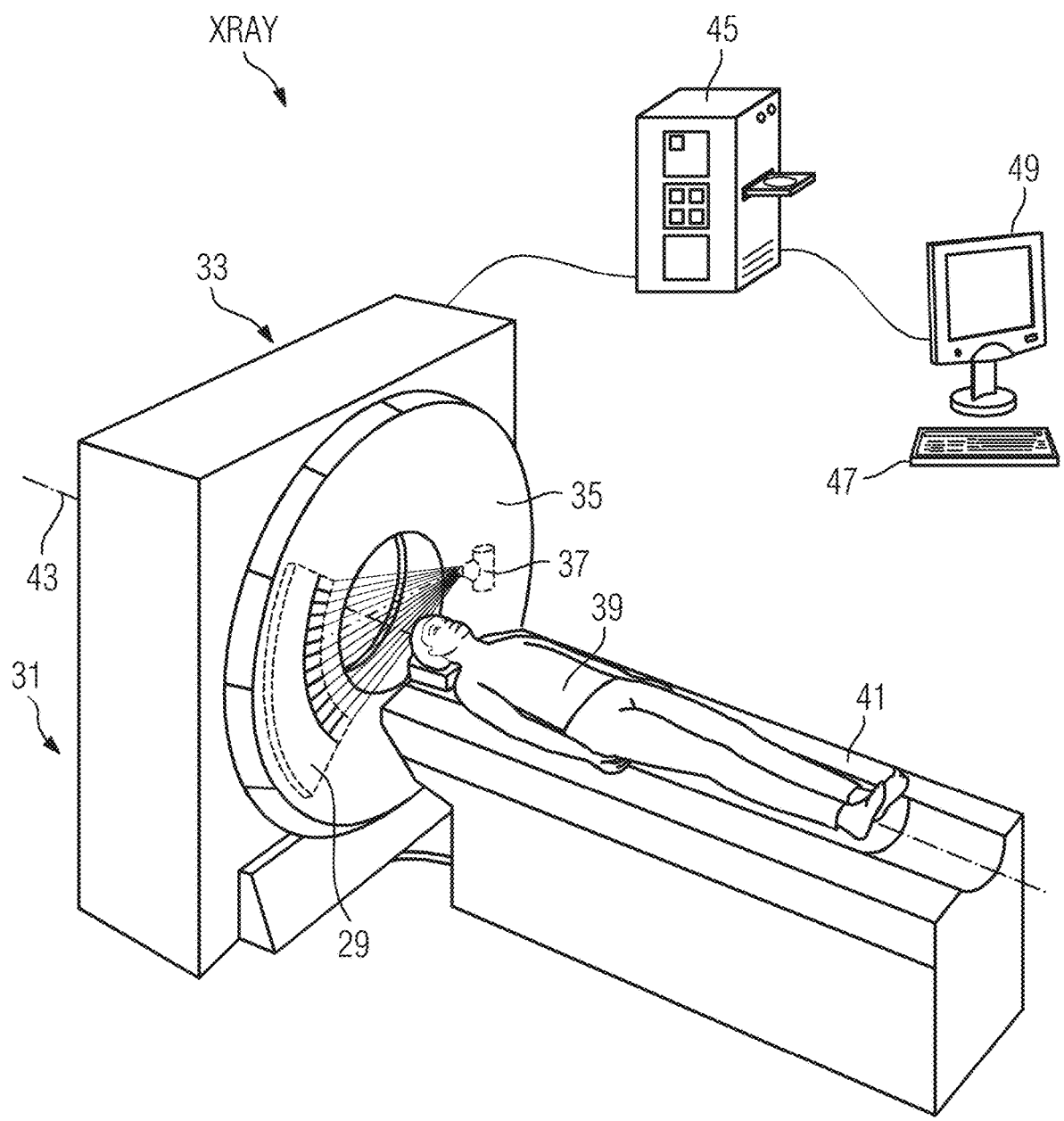
FIG. 7 shows an example of an X-ray based imaging application.

FIG. 7 shows an example of a setup for an X-ray based imaging application XRAY, in which a patient 39 is imaged via a computed tomography apparatus (CT apparatus) 31. The CT apparatus 31 contains a projection measurement data acquisition-unit 33 having a rotor 35. The rotor 35 comprises an X-ray source 37 and an X-ray detector 29. The patient 39 is supported on the patient couch 41 and can be moved along the axis of rotation 43 by the projection measurement data acquisition-unit 33 for the purpose of acquiring the projection measurement data. A data processing unit 45 is used to reconstruct and analyze sectional images or volumetric images. The data processing unit 45 is designed to receive the projection measurement data from the X-ray detector 29 and to reconstruct an image dataset on the basis of the projection measurement data. The data processing unit 45 can also comprise a control system which is designed to adjust system settings of the computed tomography apparatus 31, for instance parameter settings of the X-ray tube 37. An input facility 47 and an output unit 49 are connected to the data processing unit 45.

The control system can be used to control the application procedure of the X-ray based imaging application, at least with regard to the computed tomography apparatus 31. In the case shown, the application procedure can comprise, for example, inter alia, the execution of various scan sequences via the computed tomography apparatus 31, which are executed successively in time, and in which the patient is repeatedly exposed to X-ray radiation.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for checking a characteristic variable of an application procedure of an X-ray based medical imaging application, the method comprising:

providing a database via a first interface, the database including a plurality of patient models, each patient model of the plurality of patient models being characterized by at least one model parameter;

selecting, via at least one processor, a subset of the plurality of patient models based on the at least one model parameter assigned to a patient model of the plurality of patient models or based on the X-ray based medical imaging application;

performing, via the at least one processor, a number of simulated application procedures of the X-ray based medical imaging application based on the subset of the plurality of patient models, wherein at least one patient model of the subset of the plurality of patient models is input into each simulated application procedure of the number of simulated application procedures;

ascertaining, via the at least one processor, a value of the characteristic variable for each simulated application procedure of the number of simulated application procedures; and outputting, via a second interface, the value of the characteristic variable for each simulated application procedure, or evaluating, via the at least one processor, based upon a target for the characteristic variable, the value of the characteristic variable for each simulated application procedure, wherein the characteristic variable is checked based on the outputting or based on the evaluating.

2. The method of claim 1, wherein the method includes the evaluating, wherein in the evaluating, a case of non-compliance with the target for the characteristic variable for a current value of the characteristic variable is determined based upon a comparison between the current value and the target, and wherein the current value is a value ascertained for a respective simulated application procedure from among the number of simulated application procedure.

3. The method of claim 2, further comprising:
linking, via the at least one processor, the case of non-compliance of the current value of the characteristic variable to the at least one model parameter of a patient model input into the simulated application procedure, wherein the linking includes determining a correlation between the at least one model parameter and the case of non-compliance.

4. The method of claim 3, wherein the linking includes at least one of a machine learning technique or a cluster analysis technique.

5. The method of claim 3, wherein the application procedure of the X-ray based medical imaging application is influenced by at least one application parameter, and the method further comprises:
determining, via the at least one processor a proposed adjustment for adjusting the at least one application parameter based upon the correlation, wherein adjusting the at least one application parameter based on the proposed adjustment prevents the case of non-compliance with the target for the characteristic variable.

6. The method of claim 5, further comprising:
adjusting, via the at least one processor, the at least one application parameter based upon the proposed adjustment, and wherein, subsequent to the adjusting, at least the performing, the ascertaining, and the evaluating are carried out based upon the at least one application parameter.

7. The method of claim 1, further comprising:
storing, via a memory, at least one of a current value of the characteristic variable ascertained for a respective simulated applicating procedure, or a result of the evaluating of the current value, the at least one of the current value of the result of the evaluatingof the current value being stored in association with a patient model input into the respective simulated application procedure.

8. The method of claim 1, further comprising:
combining at least two patient models of the plurality of patient models into a combined patient model, and wherein the performing includes inputting the combined patient model into at least one simulated application procedure of the number of simulated application procedures.

9. The method of claim 1, wherein the characteristic variable is a dose characteristic variable, the dose characteristic variable characterizing the X-ray based medical imaging application in terms of an applied radiation dose, or wherein the characteristic variable is a time characteristic variable, the time characteristic variable characterizing at least one of a duration of the application procedure of the X-ray based medical imaging application or a duration of subunits of the application procedure of the X-ray based medical imaging application.

10. The method of claim 1, wherein the at least one model parameter of a particular patient model of the plurality of patient models is based on a parameter of clinical data of a patient, the parameter of the clinical data of the patient being at least one of an anatomical feature, a soft-tissue equivalent thickness, a cardiac parameter, an ECG value, a respiratory curve, a test result, or an age of the patient.

11. The method of claim 1, wherein the selecting of the subset of the plurality of patient models is based upon a comparison of a value of the characteristic variable and a measured value of the characteristic variable.

12. A checking device for checking a characteristic variable of an application procedure of an X-ray based medical imaging application, the checking device comprising:
a first interface configured to provide a database, the database including a plurality of patient models, each patient model of the plurality of patient models being characterized by at least one model parameter; and
a processing unit configured to
select a subset of the plurality of patient models based upon the at least one model parameter assigned to the patient model of the plurality of patient models or based upon the X-ray based medical imaging application;
perform a number of simulated application procedures of the X-ray based medical imaging application based upon the subset of the plurality of patient models, wherein at least one patient model of the subset of the plurality of patient models is input into each simulated application procedure of the number of simulated application procedures;
ascertain a value of the characteristic variable for each simulated application procedure of the number of simulated application procedures; and
convey the value of the characteristic variable for each simulated application procedure, to a second interface,
or
evaluate, based upon a target for the characteristic variable, the value of the characteristic variable for each simulated application procedure.

13. The checking device of claim 12, wherein
the processing unit is configured to determine a case of non-compliance with the target for the characteristic variable for a current value of the characteristic variable based upon a comparison between the current value and the target,
the current value is a value ascertained for a respective simulated application procedure from among the number of simulated application procedures,
the application procedure of the X-ray based medical imaging application is influenced by at least one application parameter, and
the processing unit is configured to
link the case of non-compliance of the current value of the characteristic variable to the at least one model parameter of a patient model input into the respective simulated application procedure wherein linking the case of non-compliance includes determining a correlation between the at least one model parameter and the case of non-compliance,
determine a proposed adjustment for adjusting the at least one application parameter based upon the correlation, wherein adjusting the at least one application parameter based upon the proposed adjustment prevents the case of non-compliance, and
adjust the application procedure based upon the proposed adjustment.

14. A non-transitory machine readable medium storing executable instructions that, when executed by one or more processors, configure the one or more processors to cause a checking device to:
provide a database, the database including a plurality of patient models, each patient model of the plurality models being characterized by at least one model parameter,
select a subset of the plurality of patient models based upon the at least one model parameter assigned to a patient model of based upon an X-ray based medical imaging application;
perform a number of simulated application procedures of the X-ray based medical imaging application based upon the subset of the plurality of patient models, wherein at least one patient model of the subset of the plurality of patient models in input into each simulated application procedure of the number of simulated application procedures;
ascertain a value of the characteristic variable for each simulated application procedure of the number of simulated application procedures; and
output the value of the characteristic variable for each simulated application procedure, or
evaluate based upon a target for the characteristic variable, the value of the characteristic variable for each simulated application procedure, wherein
the characteristic variable is checked based upon the outputting or based upon the evaluating.

15. A checking device for checking a characteristic variable of an application procedure of an X-ray based medical imaging application, the checking device comprising:
one or more processors; and
a memory storing executable instructions that, when executed by the one or more processors, is configured to cause the checking device to
provide a database, the database including a plurality of patient models, each patient model of the plurality of patient models being characterized by at least oe model parameter,
select a subset of the plurality of patient models based upon the at least one model parameter assigned to a patient model or based upon an X-ray based medical imaging application,
perform a number of simulated application procedures of the X-ray based medical imaging application based upon the subset of the plurality of patient models, wherein at least one patient model of the subset of the plurality of patient models is input into each simulated application procedure of the number of simulated application procedures,
ascertain a value of a characteristic variable for each simulated application procedure of the number of simulated application procedures, and
output the value of the characteristic variable for each simulated application procedure, or
evaluated, based upon a target for the characteristic variable, the value of the characteristic variable for each simulated application procedure, wherein
the characteristic variable is check based upon the outputting or based upon the evaluating.

16. The method of claim 4, wherein the application procedure of the X-ray based medical imaging application is influenced by at least one application parameter, and wherein the method further comprises:
determining, via the at least one processor a proposed adjustment for adjusting the at least one application parameter based upon the correlation, wherein adjusting the at least one application parameter based upon the proposed adjustment prevents the case of non-compliance with the target for characteristic variable.

17. The method of claim 16, further comprising:
adjusting, via the at least one processor, the at least one application parameter based upon the proposed adjustment, and wherein, subsequent to the adjusting, at least the performing, the ascertaining, and the evaluating are carried out based upon the at least one application parameter.

18. The method of claim 10, wherein the at least one model parameter of a particular patient model of the plurality of patient models is at least one of the anatomical feature, the soft-tissue equivalent thickness, the cardiac parameter, the ECG value, the respiratory curve, the test result, or the age of the patient.

19. A checking device for checking a characteristic variable of an application procedure of an X-ray based medical imaging application, the checking device comprising:
a first interface configured to provide a database, the database including a plurality of patient models, each patient model of the plurality of patient models being characterized by at least one model parameter; and
at least one processor configured to
select a subset of the plurality of patient models based upon the at least one model parameter assigned to a patient model of the plurality of patient models or based upon the X-ray based medical imaging application,
perform a number of simulated application procedures of the X-ray based medical imaging application based upon the subset of the plurality of patient models selected, at least one patient model of the subset of the plurality of patient models being input into each simulated application procedure of the number of simulated application procedures,
ascertain a value of the characteristic variable for each simulated application procedure of the number of simulated application procedures, and convey the value of the characteristic variable to a second interface, or evaluate, based upon a target for the characteristic variable, the value of the characteristic variable for each simulated application procedure.

20. The checking device of claim 19, wherein the at least one processor is configured to determine a case of non-compliance with the target for the characteristic variable for a current value for the characteristic variable based upon a comparison between the current value and the target, the current value is a value ascertained for a respective simulated application procedure from among the number of simulated application procedure, the application procedure of the X-ray based medical imaging application is influenced by at least one application parameter, and the at least one processor is configured to:

link the case of non-compliance of the current value to the at least one model parameter of a patient model input into the respective simulated application procedure wherein linking the case of non-compliance includes determining a correlation between the at least one model parameter and the case of non-compliance, determine, based upon the correlation, a proposed adjustment for adjusting the at least one application parameter, wherein adjusting the at least one application parameter based upon the proposed adjustment prevents the case of non-compliance; and adjust the application procedure based upon the proposed adjustment.

* * * * *